(12) United States Patent
Winsauer

(10) Patent No.: US 6,450,806 B2
(45) Date of Patent: Sep. 17, 2002

(54) ORTHODONTIC EXPANSION SCREW

(76) Inventor: Heinz Winsauer, Bahnhofstrasse 29, A-6900 Bregenz (AT)

( * ) Notice: Subject to any disclaimer, the term of this patent is extended or adjusted under 35 U.S.C. 154(b) by 0 days.

(21) Appl. No.: 09/891,706

(22) Filed: Jun. 26, 2001

(30) Foreign Application Priority Data

Jun. 27, 2000 (DE) .......................................... 100 31 300

(51) Int. Cl.[7] .............................................. A61C 3/00
(52) U.S. Cl. ........................................................ 433/7
(58) Field of Search ............................................ 433/7

(56) References Cited

U.S. PATENT DOCUMENTS

| | | | |
|---|---|---|---|
| 3,529,353 A | * | 9/1970 | Schiaroli ........................ 433/7 |
| 3,835,540 A | * | 9/1974 | Biederman ..................... 433/7 |
| 4,026,023 A |   | 5/1977 | Fisher ............................ 433/7 |
| 4,045,871 A |   | 9/1977 | Nelson ........................... 433/7 |
| 5,769,631 A | * | 6/1998 | Williams ........................ 433/7 |
| 5,885,290 A | * | 3/1999 | Guerrero et al. ............... 433/7 |

FOREIGN PATENT DOCUMENTS

| | | |
|---|---|---|
| EP | 0 919 207 | 6/1999 |
| WO | WO 94/26196 | 11/1994 |
| WO | WO 97/15241 | 5/1997 |

* cited by examiner

*Primary Examiner*—John J. Wilson
(74) *Attorney, Agent, or Firm*—Baker & Daniels

(57) ABSTRACT

The invention relates to an orthodontic expansion screw for the generation of an expansion force between a first and a second fastening elements, for the fastening to oppositely lying sides of the upper jaw, and an adjusting element connected with the fastening elements for the alteration of the mutual spacing of the fastening element. The invention is characterized in that each fastening element has at least two mounting wires with at least three free ends of the anchoring of teeth of the upper jaw.

7 Claims, 2 Drawing Sheets

Figure 4:
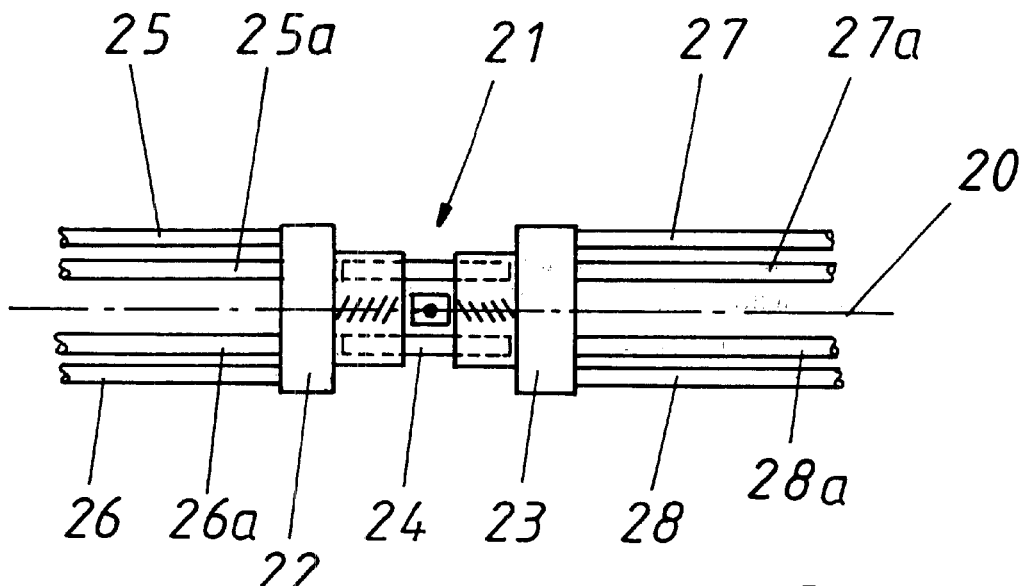

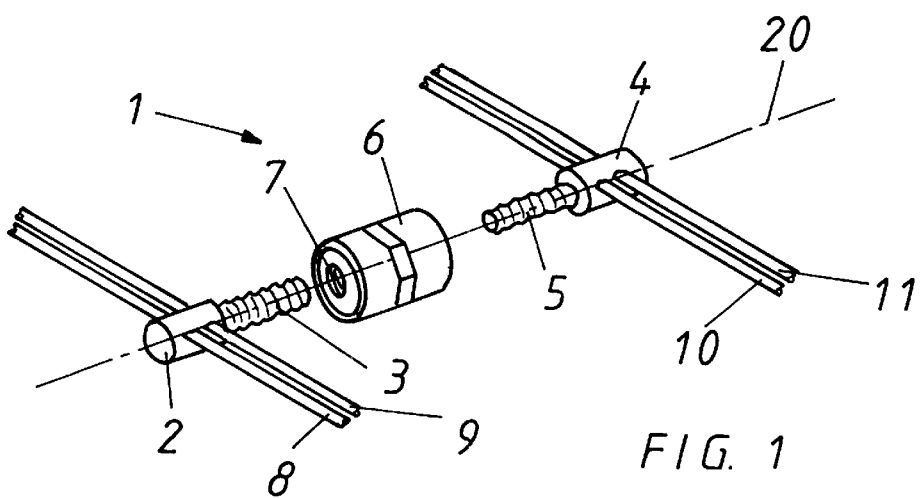
FIG. 1
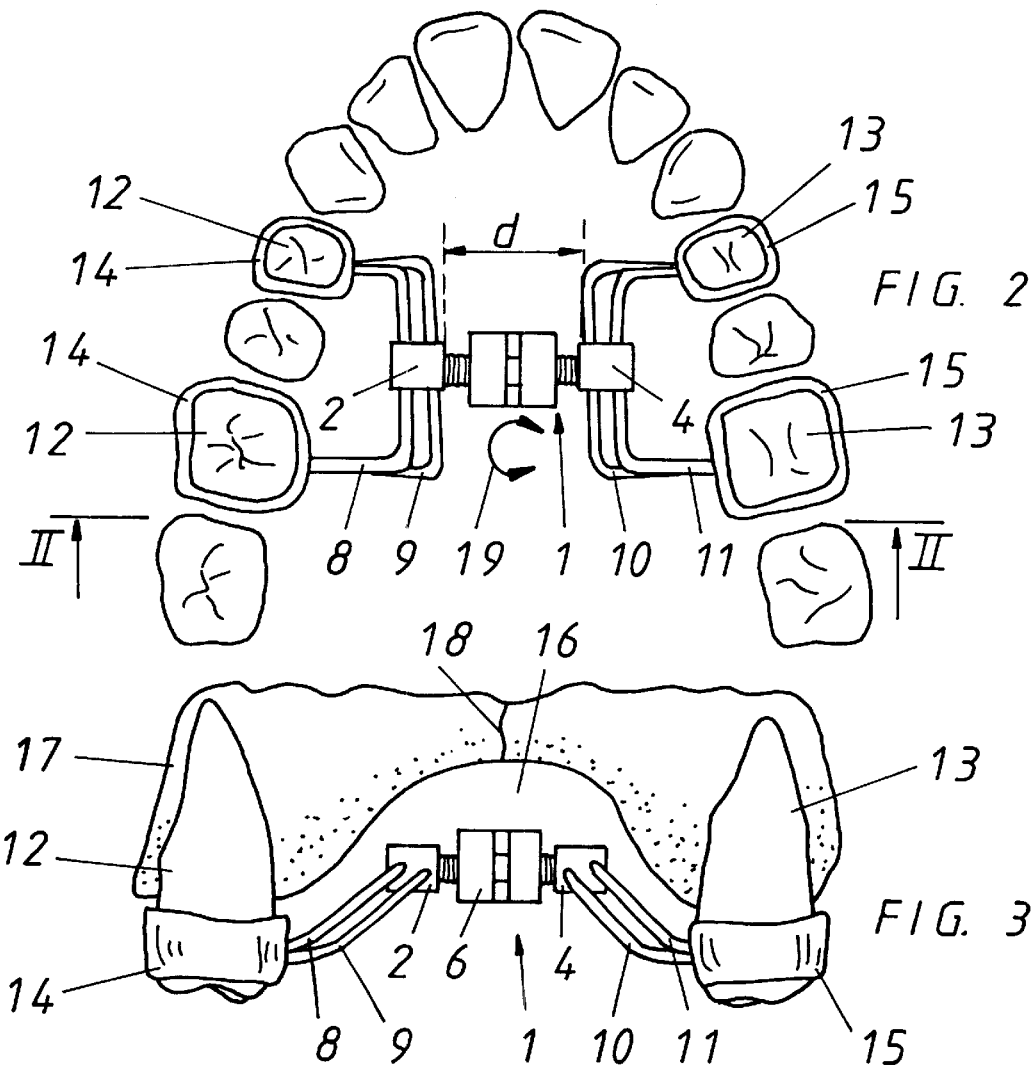
FIG. 2
FIG. 3

ORTHODONTIC EXPANSION SCREW

The invention relates to an orthodontic expansion screw for the generation of an expansion force between oppositely lying sides of the upper jaw, according to the generic term of patent claim 1.

The use of such expansion screws is well known in orthodontics. Expansion screws serve for the palatal suture widening for the skeletal widening of the upper jaw. Expansion screws of the type mentioned are disclosed, for example, in the patent documents WO-97/15241 A1; EP 0 706 349 B1; and U.S. Pat No. 4,045,871. In general, an expansion screw comprises a first and a second fastening elements to be fastened to oppositely lying sides of the upper jaw, and an adjusting element connected with these, by means of which the reciprocal spacing of the fastening elements is adjustable. For the anchoring of the fastening elements to oppositely lying teeth of the upper jaw there serve as a rule mounting wires. for the anchoring onto the teeth there is used in each case a mounting wire with two free ends per fastening unit.

Especially in patients of advanced age, the expansibility of the palatal suture decreases, and considerable forces must be applied in order to achieve any expansion at all. There, great forces act on the expansion screw and forces as well as torques act on the mounting wires which not infrequently bend in an undesired manner under the load, so that the effect of the expansion screw is lessened or entirely lost.

Underlying the invention, therefore, is the problem higher loads and with which an increased force effect can be exerted on the upper jaw for the expansion, without deformation of the mounting wires.

This problem is solved by the features given in claim 1.

According to the invention, each fastening element has at least two mounting wires with at least three free ends for the anchoring to teeth of the upper jaw.

Therewith there is yielded the advantage that per fastening element there are available at least three, preferably however, four anchoring points on the upper jaw, whereby the achievable force and torsional action on the upper jaw and the loadability of the expansion screw are altogether increased. There, the structure form o the fastening element and on/f the adjusting element is not the essential feature. These parts can be present in any known or novel construction form.

Further embodiment and modifications of the invention are yielded for the dependent patent claims.

Thus the mounting wires of each fastening element are preferably arranged at mutual spacing from one another on the respective fastening element. The mounting wires can be arranged adjacently or also one over another on the respective fastening element.

The in each case like-aligned free ends of the mounting wires in the starting state are directed about parallel to the longitudinal axis of the expansion screw. They can also be directed, however, about perpendicularly to the longitudinal axis of the expansion screw.

So that the expansion screw, especially the transition between the fastening elements and he mounting wires, will withstand heavy loads, the mounting wires are advantageously joined firmly with the fastening elements by welding, soldering or clamping.

Examples of execution of the invention are described in detail in the following with reference to the drawing figures. For the drawing and the specification there are h/yielded further features, advantages and applications of the invention.

Figure 5:
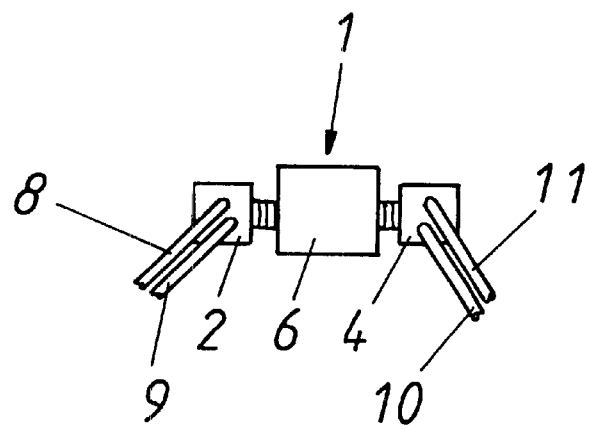

In the drawing:

FIG. 1 shows a perspective exploded representation of the expansion screw;

FIG. 2 a view of the upper jaw teeth with installed expansion screws;

FIG. 3 a view of the upper jaw with installed expansion screw cut along line II—II in FIG. 1;

FIG. 4 schematically another form of execution of the expansion screw;

FIG. 5 schematically a further form of execution of the expansion screw with mounting wires lying one over another.

FIG. 1 shows an example of execution of an expansion screw 1 according to the invention. the expansion screw 1 comprises essentially a "left" fastening element 2 and a "right" fastening element 4, which are both joined with one another over an adjusting element 6. The elements 2, 4, and 6 are cylindrically constructed, but can also have an arbitrary other shape. Tho construction forms of the fastening elements and of the adjusting element are not essential for the invention.

The fastening element 2, 4 have threaded members 3, 5, which can be screwed into allocated bores 7 of the adjusting element 6. The bores 7 are located on oppositely lying face sides of tho adjusting element 6. The threaded pieces 3, 5 have counter-rotating threads, the allocated bores 7 in the adjusting element 6 being correspondingly constructed. By rotating the adjusting element 6 in arrow direction 19 (FIG. 2), the mutual spacing d of the fastening elements 2, 4 can be altered.

The elements 2, 4 and 6 are arranged along an axis 20.

In the example of execution shown, to each fastening element 2, 4 according to the invention there are fastened two mounting wires 8, 9 and 10, 11, respectively, with four free ends lying adjacently. The mounting wires 8 to 11 are preferably led through bores of the fastening elements 2, 4, and welded or soldered with these; but they can also be welded or soldered directly onto the fastening elements.

In the starting state the mounting wires 8, 9 and 10, 11, respectively, run parallel and at a distance from one another, about perpendicularly to the axis 20.

FIGS. 2 and 3 show the expansion screw 1 of he invention installed in the palatine space 16 of the upper jar 17. The expansion screw 1 is arranged by the orthodontist individually for each patient in his palatine space 16, a force being exerted between the oppositely lying sides of the upper jaw in order to enlarge the palatal suture 18, which is used for a correction of the tooth positions of the upper jaw.

For this the free ends of the pairs of mounting wires 8, 9 and 10, 11, respectively, are correspondingly bent and fastened in each case to oppositely lying tooth anchorings 14 and 15, respectively. The tooth anchorings 14, 15 are again firmly joined with teeth 12 and 13 of the upper jaw 17. Other types of anchorings to the upper jaw 17 and to the teeth are likewise possible.

By a rotating of the adjusting element 6 in arrow direction 19, the reciprocal spacing of the fastening elements 2, 4 and therewith the action force of the expansion screw 1 on the upper jaw 17 can be altered and individually adjusted for each patient.

For the maximal stability of the arrangements of the mounting wires 8, 9 and 10, 11, respectively, there—proceeding from the fastening elements 2, 4—are bent in such manner that the free ends of the wires 8, 9 and 10, 11, respectively, allocated to one another, preferably meet in a point of the allocated tooth anchorings 14, 16. In this manner there arises a "triangle of forces" which withstands heavy loads, so that greater forces can be exerted on the upper jaw 17 that are possible with conventional expansion screws.

Alternatively, the ends of the wires allocated to one another may not meet in a point, so that a "force parallelogram" arises, which likewise delivers the stability advantages described.

FIG. 4 shows a modified formation of an expansion screw 21 according to the invention, with an adjusting element 24 and two fastening elements 22, 23, in which—in distinction from tho variant according to FIGS. 1 to 3—eight mounting wires 25, 25a, 26, 26a, 27 27a, 28, 28a are used. On each fastening element 22, 23 there are arranged in each case four mounting wires, which in starting position run about parallel to the axis 20 of the expansion screws.

FIG. 5 shows a further variant of the expansion screw 1, in which the mounting wires 8–11 are arranged one over another on the fastening elements 2, 4.

Legends for Drawings

1. Expansion screw
2. Fastening element
3. Threaded member
4. Fastening element
5. Threaded member
6. Adjusting element
7. Threaded bore
8. Mounting wire
9. Mounting wire
10. Mounting wire
11. Mounting wire
12. Tooth
13. Tooth
14. Tooth anchoring
15. Tooth anchoring
16. Palatine space
17. Upper jaw
18. Palatorrhaphy/palatal suture
19. Rotation direction
20. Longitudinal axis
21. Expansion screw
22. Fastening element
23. Fastening element
24. Adjusting element
25. Mounting wire, 25a
26. Mounting wire, 26a
27. Mounting wire, 27a
28. Mounting wire, 28a Spacing

What is claimed is:

1. An orthodontic expansion screw for the generation of an expansion force between oppositely lying sides of the upper jaw, with a first and a second fastening elements for fastening to oppositely lying sides of the upper jaw, and an adjusting element connected with the fastening elements for the alteration of the reciprocal spacing of the fastening elements, each fastening element having at least two mounting wires with at least three free ends for an anchoring to the teeth of the upper jaw, wherein in each case like-aligned free ends of the mounting wires are brought together in a common point on the tooth anchoring.

2. Expansion screw according to claim 1, characterized in that the mounting wires of each fastening element are arranged at a reciprocal spacing from one another on the respective fastening element.

3. Expansion screws according to claim 1, characterized in that the mounting wires in the unbent state are aligned about parallel to the longitudinal axis of the expansion screw.

4. Expansion screw according to claim 1 characterized in that the mounting wires are firmly joined with the fastening arrangements by welding, soldering, clamping or chemical bonding.

5. An orthodontic expansion screw for the generation of an expansion force between oppositely lying sides of the upper jaw, with a first and a second fastening elements for fastening to oppositely lying sides of the upper jaw, and an adjusting element connected with the fastening elements for the alteration of the reciprocal spacing of the fastening elements, each fastening element having at least two mounting wires with at least three free ends for an anchoring to the teeth of the upper jaw, wherein in each case like-aligned free ends of the mounting wires are brought together at a common tooth anchoring.

6. Expansion screws according to claim 5, characterized in that the mounting wires in the unbent state are aligned about parallel to the longitudinal axis of the expansion screw.

7. Expansion screw according to claim 5, characterized in that the mounting wires are firmly joined with the fastening arrangements by welding, soldering, clamping or chemical bonding.

* * * * *